United States Patent
Schaal

(10) Patent No.: US 6,346,217 B1
(45) Date of Patent: Feb. 12, 2002

(54) COMPOSITION AND METHOD FOR CLEANING DRINK WATER TANKS

(75) Inventor: Christian Schaal, Nettetal (DE)

(73) Assignee: Water Whole International, Inc., Norman, OK (US)

( * ) Notice: Subject to any disclaimer, the term of this patent is extended or adjusted under 35 U.S.C. 154(b) by 0 days.

(21) Appl. No.: 09/324,383

(22) Filed: Jun. 2, 1999

(51) Int. Cl.$^7$ ................................................. A01N 1/00
(52) U.S. Cl. ............................... 422/28; 422/5; 422/12; 422/28; 252/8.8; 252/146
(58) Field of Search ................................ 422/5, 28, 8.8, 422/12; 252/146; 562/541, 605

(56) References Cited

U.S. PATENT DOCUMENTS

| | | | |
|---|---|---|---|
| 3,644,204 A | * 2/1972 | Heins et al. | 252/8.8 |
| 3,959,168 A | 5/1976 | Germscheid et al. | 252/180 |
| 4,199,469 A | * 4/1980 | Walzer | 252/146 |
| 4,434,069 A | 2/1984 | Fairchild | 252/174.14 |
| 4,439,339 A | 3/1984 | Doumit | 252/80 |
| 4,857,225 A | 8/1989 | Terada et al. | 252/100 |
| 5,068,415 A | * 11/1991 | von Werner et al. | 562/541 |
| 5,360,488 A | 11/1994 | Hieatt et al. | 134/22.11 |
| 5,451,335 A | 9/1995 | Hieatt et al. | 252/82 |
| 5,527,395 A | 6/1996 | Perry et al. | 134/3 |
| 5,786,313 A | 7/1998 | Schneider et al. | 510/219 |
| 5,891,392 A | 4/1999 | Monticello et al. | 422/28 |
| 6,106,774 A | 8/2000 | Monticello et al. | 422/28 |

FOREIGN PATENT DOCUMENTS

| | | |
|---|---|---|
| DE | 25 20 988 A1 | 11/1975 |
| DE | 42 21 457 A1 | 1/1994 |
| EP | 0 379 256 A2 | 7/1990 |
| EP | 0 456 272 A1 | 11/1991 |
| EP | 0 656 417 A1 | 6/1995 |
| WO | WO 96/17918 | 6/1996 |
| WO | WO 97/15649 | 5/1997 |
| WO | WO 97/39986 | 10/1997 |

* cited by examiner

Primary Examiner—Robert J. Warden, Sr.
Assistant Examiner—Imad Soubra
(74) Attorney, Agent, or Firm—Brent A. Capehart; Gable & Gotwals

(57) ABSTRACT

A composition and method for cleaning drink water tanks. The composition contains in combination amidosulfonic acid, nitrilotriacetic acid, isopropanol and water. The composition is applied to deposit which have formed on the walls and other internal surfaces of a drink water tank.

6 Claims, No Drawings

COMPOSITION AND METHOD FOR CLEANING DRINK WATER TANKS

REFERENCE TO PENDING APPLICATIONS

This application is not related to any pending applications.

REFERENCE TO MICROFICHE APPENDIX

This application is not referenced in any microfiche appendix.

BACKGROUND OF THE INVENTION

This invention relates generally to the cleaning of drink water tanks and more particularly, to the removal of particular types of deposits formed along the walls and other internal surfaces of drink water tanks.

Typically the water level of a drink water tank rises and falls with demand. The walls of the drink water tank are therefore constantly being exposed to air and water. This causes a biological film, such as algae and microorganisms, along with incrustations such as calcium, iron and manganese to form deposits along the surface of the wall.

Cleaning these deposits from the wall has been the subject of a number of prior art compositions. U.S. Pat. No. 4,199,469 issued to Waltzer on Apr. 22, 1980 discloses a composition and method for cleaning drink water tanks. This composition utilizes a group of acids (ascobic, formic, phosphoric, citric and hydrochloric). Given the number of constituents the composition is complicated and confusing. Therefore, there exists a need for a more simple composition in order to clean drink water tanks.

BRIEF SUMMARY OF THE INVENTION

In its composition aspect the present invention involves a composition comprising amidosulfonic acid in the range of 4 to 30 percent by weight, nitrilotriacetic acid in the range of 0.1 to 0.2 percent by weight, isopropanol in the range of 0.1 to 0.5 percent by weight with the balance of the composition consisting of water.

The composition is applied to the internal surfaces of a drink water tank having deposits thereon. The solution loosens the adhesion between the deposits and the surface at which time the composition and deposits are rinsed away. Further, the biological film is reliably eliminated.

The composition can be added to a disinfectant solution made of peroxoacetic acid. This allows the internal surface to be cleaned and disinfected during the same procedure.

It is a primary object of the invention to provide a composition and method for cleaning drink water tanks that avoids the problems mentioned above.

Another object of the invention is to provide a solution for cleaning and disinfecting drink water tanks.

Other objects and further scope of the applicability of the present invention will become apparent from the detailed description to follow wherein like parts are designated by like reference numerals.

DETAILED DESCRIPTION OF THE PREFERRED EMBODIMENTS

The preferred embodiment of the present invention is directed toward the cleaning of drink water tanks specifically for the removal of deposits which have formed along the surface of the walls of a drink water tank. One basic formula is:

| Ingredients | Range (Weight Percentage) | |
|---|---|---|
| | Broad | Preferred |
| Amidosulfonic Acid | 4–30% | 10% |
| Nitrilotriacetic Acid | 0.1–0.2% | 0.15% |
| Isopropanol | 0.1–0.5% | 0.3% |
| Water | Balance | Balance |

The composition of the preferred embodiment of the present invention is applied to the surface of the walls of a drink water tank where deposits have formed. These deposits comprise the combination of a biological film, such as algae and microorganisms, with sediments, such as calcium, iron and/or manganese. The composition of the preferred embodiment loosens the adhesive bond between the deposits and the wall surface allowing for the removal thereof. The composition is then rinsed away along with the loosened deposits as well as any remaining biological film.

In an additional embodiment, the composition is mixed with a disinfectant solution made of peroxoacetic acid in the range of 0.5 to 5.0% by weight. This embodiment is able to provide the cleaning ability of the above composition along with a disinfectant ability of the peroxoacetic acid.

It is to be understood that the above description is illustrative only and not limiting of the disclosed invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. A method of cleaning deposits from a surface of a drink water tank, said method comprising the steps of:

creating a cleaning composition from a cleaning solution and a disinfectant solution, said cleaning solution consisting of between 6.00 and 15.00 weight percent amidosulfamic acid, between 0.10 and 20.00 weight percent nitrilotriacetic acid, between 0.10 and 0.50 weight percent isopropanol and the balance of said cleaning solution consisting of water;

applying said cleaning composition to said surface; and rinsing said surface with water in order to remove said deposits from said surface.

2. The method of claim 1 wherein said composition is applied to said surfaces by pressurized spraying.

3. The method of claim 2 wherein said composition is applied to said surfaces by pressurized spraying.

4. The method of claim 2 wherein said composition is applied to said surfaces by low pressurized spraying.

5. The method of claim 1 wherein said components are in the relative weight percent proportions:

about 10.00 percent amidosulfamic acid;

about 0.15 percent nitrilotriacetic acid;

about 0.30 percent isopropanol.

6. The method of claim 5 wherein the balance of said solution consisting of demineralized water.

* * * * *